US006206001B1

(12) United States Patent
Garber et al.

(10) Patent No.: US 6,206,001 B1
(45) Date of Patent: Mar. 27, 2001

(54) RESPIRATOR SELECTION PROGRAM

(75) Inventors: Sharon R. Garber, Crystal; Craig E. Colton; Larry L. Janssen, both of Stillwater, all of MN (US)

(73) Assignee: Minnesota Mining and Manufacturing Company, St. Paul, MN (US)

( * ) Notice: Subject to any disclaimer, the term of this patent is extended or adjusted under 35 U.S.C. 154(b) by 300 days.

(21) Appl. No.: 08/648,790

(22) Filed: May 16, 1996

(51) Int. Cl.[7] .................................................. G06F 15/20
(52) U.S. Cl. ............................... 128/204.21; 128/201.22
(58) Field of Search ................................. 128/716, 719, 128/727, 730, 863, 857, 201.22–201.24, 204.17, 204.21; 364/413.01–413.03

(56) References Cited

U.S. PATENT DOCUMENTS

| | | | |
|---|---|---|---|
| 4,459,266 | * | 7/1984 | Lamoreaux ........................... 128/719 |
| 4,491,725 | * | 1/1985 | Pritchard ........................ 364/413.01 |
| 4,858,121 | * | 8/1989 | Barber et al. .................... 364/413.01 |
| 4,860,223 | * | 8/1989 | Grilk ............................... 364/413.01 |
| 5,574,828 | * | 11/1996 | Hayward et al. ................ 364/413.02 |

OTHER PUBLICATIONS

Computer software program (1 diskette) entitled *Guide to Chemical–Resistant Best Gloves*, @ 1993 by Best Manufacturing Company, Menlo, GA.
Computer Software publications catalog for Chemical Protective Clothing Permeation/Degradation Database, ACGIH, undated, (pp. 48, 52).
Product advertisement for *"SpecWare,"* undated, 1 page.
Product advertisement for "Sax's Dangerous Properties of Industrial Materials" (Eight Edition) and *"Hawley's Condensed Chemical Dictionary"* (Twelfth Edition), by Richard J. Lewis, Sr., pub. by Van Nostrand Reinhold, NY, NY, undated, 1 page.
Product information sheet for "Best Glove Recommendations For Vinyl Chloride (GAS)", dated Jun. 2, 1993, 1 page.
Photocopy of 3M Occupational Health and Environmental Safety Division brochure with page titles "3M has made the process of selecting a respirator easier and faster." and "3M Select Software© is accurate, traceable and an effective way to meet OSHA regulations.", undated, 1 page.
Photocopy of Auergesellschaft GmbH product brochure entitled "AUERDATA PR 2.0", (undated). (Translation has been ordered by Applicants' attorney and will be provided to PTO upon receipt).

* cited by examiner

Primary Examiner—Robert L. Nasser
(74) Attorney, Agent, or Firm—Marshall, O'Toole, Gerstein, Murray & Borun

(57) ABSTRACT

A respirator selection program contains a database and a non-standards based engine. The database includes at least a chemicals database, a health effects database, a standards database, and a respirator database. The chemicals database contains data on chemicals which may require the use of respirators. The chemicals database also contains pointers to the health effects database. The health effects database contains health effects resulting from exposure to the chemicals in the chemical database. The non-standards based engine, when executed, performs the steps of (a) accepting first and second chemicals which are entered by a user, (b) accepting corresponding first and second exposure amounts which are entered by the user, and (c) selecting a respirator based upon the chemicals database, the health effects database, the standards database, the respirator database, the first and second chemicals which are entered by the user, and the first and second exposure amounts which are entered by the user.

48 Claims, 5 Drawing Sheets

CHEMICALS DATABASE — 201

| NAMES | X | Y | Z | |
|---|---|---|---|---|
| EXPOSURE LIMIT | 1 | 2 | 1 | |
| GAS & VAPOR | $G_1$ | $G_3$ | $G_2$ | ... |
| HEALTH EFFECT | $H_1$ | $H_1$ | $H_2$ | |
| STANDARD TABLES | $S_1$ | $S_1$ | $S_2$ | |
| CAS # | | | | |

*Fig. 3*

GAS & VAPOR DATABASE — 202

| | |
|---|---|
| $G_1$ | $GV_1$ |
| $G_2$ | $GV_2$ |
| $G_3$ | $GV_3$ |

*Fig. 4*

GAS & VAPOR DATABASE — 203

| | |
|---|---|
| $H_1$ | CANCER CAUSING |
| $H_2$ | IRRITATION |

*Fig. 5*

FACEPIECE DATABASE

FP₁      FULL FACE
FP₂      HALF FACE
FP₃      HELMET

STANDARDS TABLES DATABASE

PHOSPHORIC ACID $S_{n-1}$

| HR | RESPIRATOR TYPE |
|---|---|
| ≤ 50 | FP₁ F₁ |
| > 50 ≤ 1000 | SA FP₁ |
| > 1000 | SCBA |

RADIONUCLIDE (PARTICULATES ONLY)

$S_n$

| HR | RESPIRATOR TYPE |
|---|---|
| ≤ 10 | F₁ |
| > 10 ≤ 50 | FP₁ F₁ |
| > 50 ≤ 1000 | FP₁ F₁ PAPR |
| > 1000 | SCBA |

RADIONUCLIDE (GAS & VAPORS OR COMBINATION GV / PARTICULATES)

$S_{n+1}$

| HR | RESPIRATOR TYPE |
|---|---|
| ≤ 50 | SA |
| > 50 ≤ 1000 | SA FP₁ |
| > 1000 | SCBA |

| RESPIRATOR DATABASE | | | |
|---|---|---|---|
| NAME | FACEPIECE | GAS & VAPOR | FILTER |
| HF OV DM | HF | OV | DM |
| HFOVDM F/F | F/F | OV | DM |

RESPIRATOR SELECTION PROGRAM

TECHNICAL FIELD OF THE INVENTION

The present invention relates to a program which facilitates a user in the selection of respirators.

BACKGROUND OF THE INVENTION

Exposure to chemical gases and vapors often requires the use of a respirator in order to avoid harmful health effects. Consequently, there are several respirator protection guidebooks currently available which provide information about potentially harmful chemicals disclosed therein. These guidebooks also designate a respirator which is intended to provide a proper level of protection for a corresponding exposure rate of a corresponding quantity of each corresponding chemical disclosed therein.

Moreover, there are software guides currently available which put the information contained in these guidebooks into a database format so that this information may be more easily searched. One example of such a software guide offered by MSA. There are similar systems for the selection of gloves such as Best Gloves, Specwear, Forsburg, and for the selection of detector tubes, such as is offered by Draeger in Germany.

These guidebooks and software guides do not facilitate the selection of respirators based upon interactions between multiple chemicals and based upon multiple levels of exposure to these chemicals. Furthermore, while there are other known software programs which do permit the selection of a respirator based upon multiple chemicals and based upon multiple levels of exposure to these chemicals, these other known software programs are rule-based systems and do not include databases. Another known system is a combination of a database system and a rule-based system. Rule-based systems, and partially rule-based systems (i.e., systems combining a database and a rule-based engine), incorporate many or most of the standards, which govern respirator selection, into a respirator selection engine. However, these fully or partially rule-based systems do not consider the health effects of the chemicals to which people are exposed during the selection of respirators. Moreover, because these fully or partially rule-based systems are rule based, they are very difficult to change. Thus, when government standards, which govern the selection of respirators, change, as they do often, considerable time and effort must be expended in order to upgrade these fully and partially rule-based systems with these standards changes.

The present invention overcomes one or more of the problems discussed above with regard to respirator selection systems.

SUMMARY OF THE INVENTION

In accordance with one aspect of the present invention, a method of selecting a respirator comprises the steps, performed by a data processing system, of (a) executing program code in the data processing system in order to determine a health effect of a first chemical, (b) executing program code in the data processing system in order to determine a health effect of a second chemical, and (c) executing program code in the data processing system in order to select a respirator based upon the health effects of the first and second chemicals.

In accordance with another aspect of the present invention, a computer readable storage medium has program code stored thereon. The program code contains a chemicals database, a standards database, and a respirator database. The chemicals database contains data on chemicals which may require the use of respirators. The standards database contains data on respirator selection related to the chemicals contained in the chemicals database. The program code further contains a non-standards based engine which, when executed, performs the steps of (i) accepting a chemical which is entered by a user, (ii) accepting an exposure amount which is entered by the user, and (iii) selecting a respirator based upon the chemicals database, the standards database, the respirator database, the chemical which is entered by the user, and the exposure amount which is entered by the user.

In accordance with yet another aspect of the present invention, a computer readable storage medium has program code stored thereon. The program code contains a chemicals database, a health effects database, a standards database, and a respirator database. The chemicals database contains data on chemicals which may require the use of respirators, and the chemicals database also contains pointers to the health effects database. The health effects database contains health effects resulting from exposure to the chemicals in the chemical database. The program code further contains a non-standards based engine which, when executed, performs the steps of (a) accepting first and second chemicals which are entered by a user, and (b) selecting a respirator based upon the chemicals database, the health effects database, the standards database, the respirator database, and the first and second chemicals which are entered by the user.

In accordance with still another aspect of the present invention, an article of manufacture comprises a computer readable storage medium and program code stored on the computer readable storage medium. The program code contains a database and a non-standards based engine. The non-standards based engine, when executed, performs the steps of (a) accepting first and second chemicals which are entered by a user, (b) accepting first and second exposure amounts which correspond to the first and second chemicals and which are entered by the user, and (c) selecting a respirator based upon the database, the first and second chemicals which are entered by the user, and the first and second exposure amounts which are entered by the user.

In accordance with a further aspect of the present invention, a computer readable storage medium has program code stored thereon. The program code includes a database containing data on chemicals and respirators, and the program code further includes a non-standards based engine. The non-standards based engine, when executed, performs the steps of (a) accepting first and second chemicals which are entered by a user, and (b) selecting a respirator based upon the database and the first and second chemicals which are entered by the user.

BRIEF DESCRIPTION OF THE DRAWING

These and other features and advantages will become more apparent from a detailed consideration of the invention when taken in conjunction with the drawing in which:

FIGS. 3–9 are examples illustrating the construction of the databases shown in FIG. 2; and, FIG. 10 is a flow diagram of a non-standards based engine which is included in the respirator selection program of the present invention and which is executed in order to select a respirator based upon the databases shown in FIG. 2.

DETAILED DESCRIPTION

Figure 1:
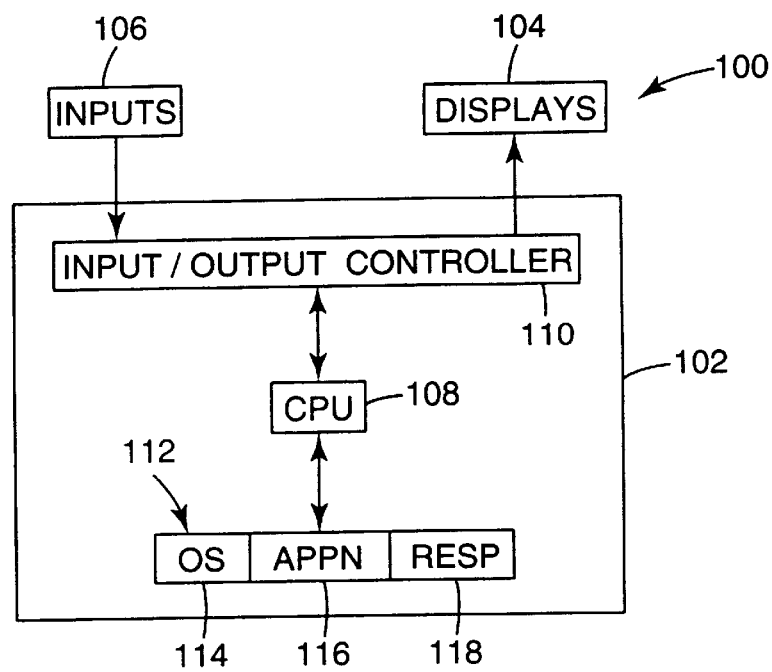
FIG. 1 is a block diagram of a data processing system which executes a respirator selection program in accordance with the present invention.

One possible operating environment of the present invention is a data processing system, such as a data processing system 100 shown in FIG. 1. The data processing system 100, for example, may be a personal computer or work station which includes a processor 102, one or more display terminals 104, and one or more input devices 106. The display terminals 104 may include, for example, a monitor having a viewing screen, a printer, and/or the like. The input devices 106 may include, for example, a mouse, a keyboard, and/or similar devices.

The processor 102 includes a central processing unit (CPU) 108 which communicates with the display terminals 104 and the input devices 106 through an input/output controller 110, and which processes program code stored in a memory 112. The program code stored in the memory 112 includes, at least in part, an operating system 114, various application programs 116, and a respirator selection program 118. The application programs 116 may include word processing programs, spread sheet programs, and the like. The respirator selection program 118 is executed by the processor 102 in order to perform the functions of the present invention.

Figure 2:
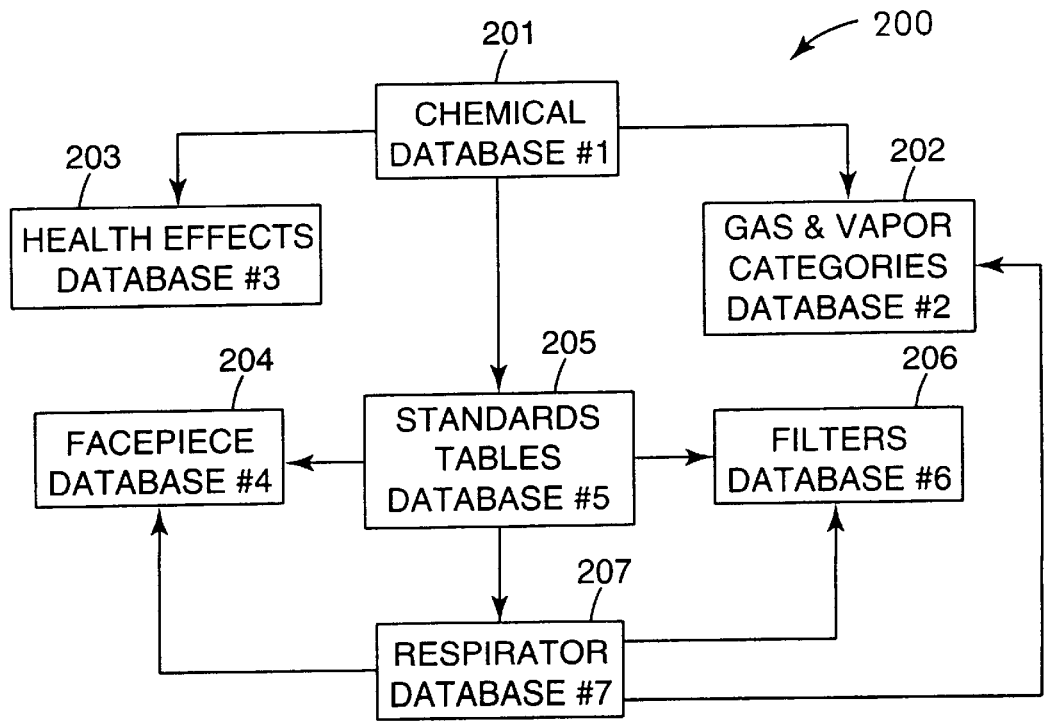
FIG. 2 illustrates the relationship between the databases included in the respirator selection program of the present invention.
Figure 10:
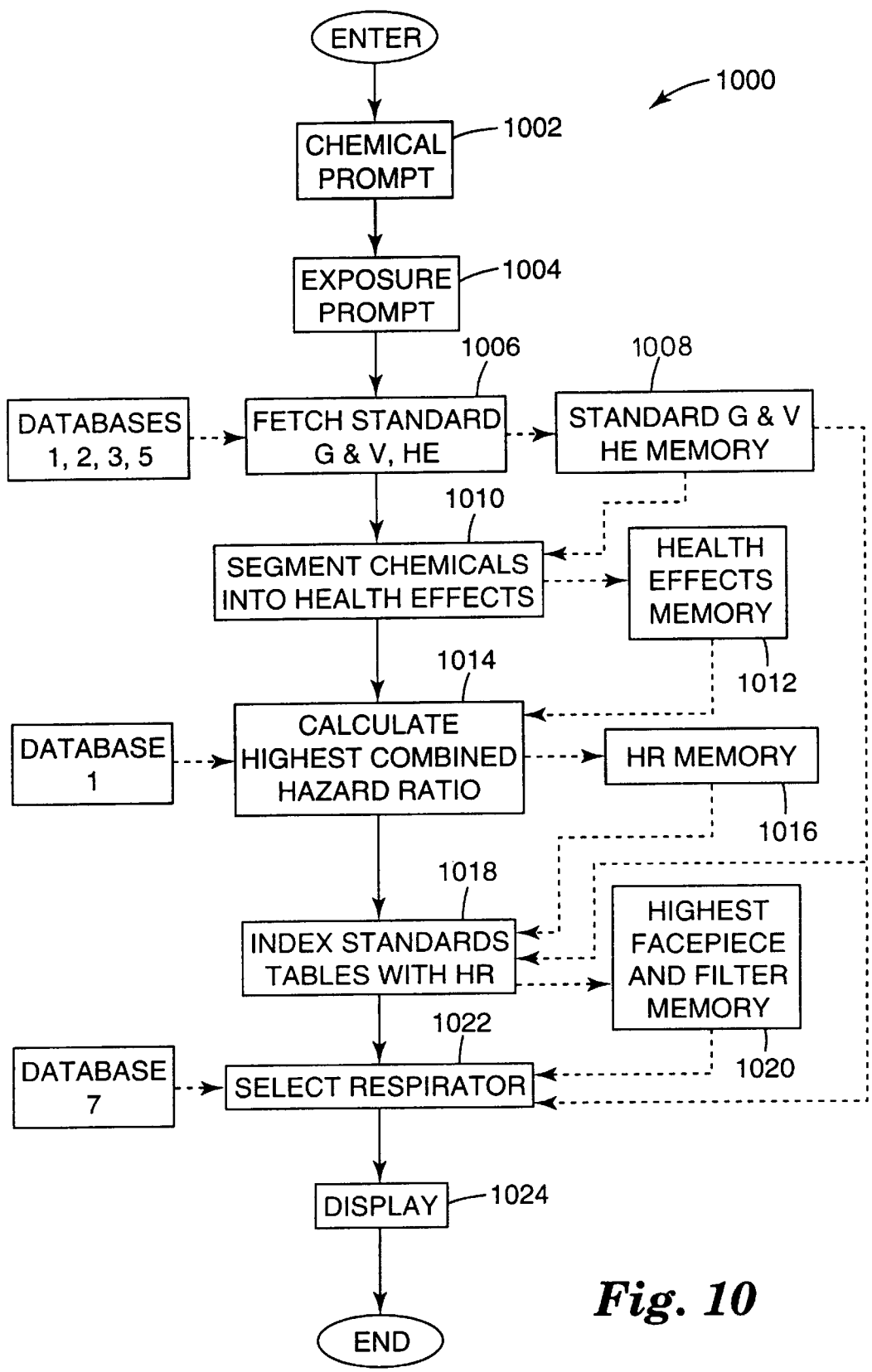

The respirator selection program 118 has a database component 200, which is illustrated in FIGS. 2–9, and a respirator selection component 1000, which is a non-standards based engine and which is illustrated in FIG. 10. The database component 200 of the respirator selection program 118, as illustrated in FIG. 2, is comprised of seven databases. These databases include a Chemicals Database 201, a Gas and Vapor Categories Database 202, a Health Effects Database 203, a Facepiece Database 204, a Standards Tables Database 205, a Filters Database 206, and a Respirator Database 207.

FIG. 2 also illustrates the interrelationship between the databases 201–207. This interrelationship is established by pointers which are contained in the database component 200 and which point from various databases to various other databases. Thus, the Chemicals Database 201 has pointers which point into the Gas and Vapor Categories Database 202, the Health Effects Database 203, and the Standards Tables Database 205. Similarly, the Standards Tables Database 205 contains pointers which point into the Facepiece Database 204, the Filters Database 206, and the Respirator Database 207, and the Respirator Database 207 contains pointers which point into the Facepiece Database 204, the Filters Database 206, and the Gas and Vapor Categories Database 202.

Examples of the databases 201–207 are illustrated in FIGS. 3–9. These examples are illustrative of the type of data which should be contained in the databases 201–207 in order to facilitate operation of the present invention. It should be understood, however, that these examples are not exhaustive of the type of data which may be contained within each of the databases 201–207, and that the data which is contained in these databases is dependent upon the particular requirements of the user and upon the standards of each country in which the present invention is used.

Accordingly, an example of the Chemicals Database 201 is illustrated in FIG. 3. This example of the Chemicals Database 201 includes data for three exemplary chemicals which are designated, for purposes of this example, as chemicals X, Y, and Z. For each such chemical, the Chemicals Database 201 includes (i) an exposure limit, which may be in parts per million and which establishes the limit to which a person may be exposed to the corresponding chemical without the need for a respirator, (ii) gas and vapor pointers $G_1, G_2, G_3, \ldots G_{n-1}, G_n, G_{n+1} \ldots$ which point into the Gas and Vapor Categories Database 202, (iii) health effects pointers $H_1, H_2, \ldots H_{n-1}, H_n, H_{n+1} \ldots$ which point into the Health Effects Database 203, (iv) standards tables pointers $S_1, S_2, \ldots S_{n-1}, S_n, S_{n+1}, \ldots$ which point into the Standards Tables Database 205, and (v) the chemical's CAS number.

The gas and vapor pointers $G_1, G_2, G_3, \ldots G_{n-1}, G_n, G_{n+1} \ldots$ point into the Gas and Vapor Categories Database 202 in order to designate the types of gases and vapors which are associated with the chemicals listed in the Chemicals Database 201. Similarly, the health effects pointers $H_1, H_2, \ldots H_{n-1}, H_n, H_{n+1} \ldots$ point into the Health Effects Database 203 in order to designate the health effects associated with exposure to a corresponding chemical and the standards tables pointers $S_1, S_2, \ldots S_{n-1}, S_n, S_{n+1} \ldots$ point into the standards tables database 205 which contains pointers to the Facepiece Database 204 and the Filters Database 206.

An example of the Gas and Vapor Categories Database 202 is illustrated in FIG. 4. The Gas and Vapor Categories Database 202 stores a listing of the gases and vapors $GV_1, GV_2, GV_3 \ldots$ which are associated with the chemicals contained in the Chemicals Database 201. These gases and vapors $GV_1, GV_2, GV_3 \ldots$ are stored in the Gas and Vapor Categories Database 202 in accordance with the gas and vapor pointers $G_1, G_2, G_3, \ldots G_{n-1}, G_n, G_{n+1} \ldots$ contained in the Chemicals Database 201.

An example of the Health Effects Database 203 is illustrated in FIG. 2. The Health Effects Database 203 stores a listing of the health effects which are associated with the chemicals contained in the Chemicals Database 201. These health effects are stored in the Health Effects Database 203 in accordance with the health effects pointers $H_1, H_2, \ldots H_{n-1}, H_n, H_{n+1} \ldots$ contained in the Chemicals Database 201.

Figures 6, 7:
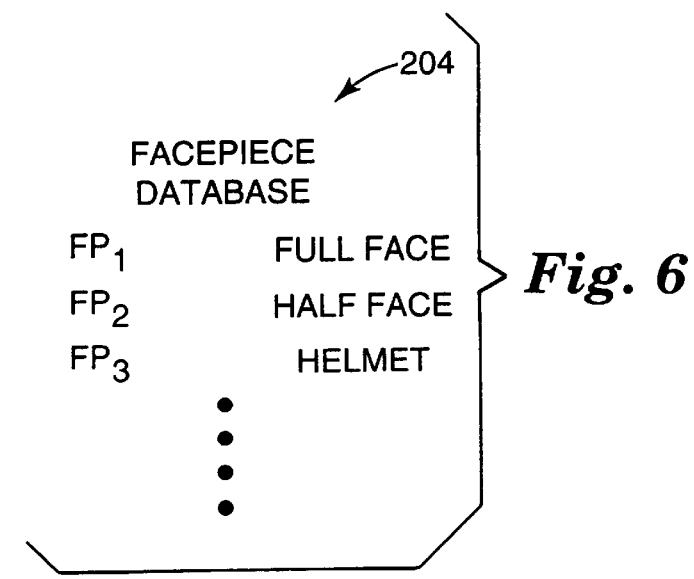

An example of the Facepiece Database 204 is illustrated in FIG. 6. The Facepiece Database 204 stores a listing of the facepieces which are available for the respirators contained in the Respirator Database 207. These facepieces are stored in the Facepiece Database 204 in accordance with facepiece pointers $FP_1, FP_2, FP_3, \ldots F_{n-1}, FP_n, FP_{n+1} \ldots$ contained in the Standards Tables Database 205.

An example of the Standards Tables Database 205 is illustrated in FIG. 7. As illustrated in FIG. 7, the Standards Tables Database 205 contains a series of standards tables which are appropriate for chemicals or groups of chemicals stored in the Chemicals Database 201. Each standards table may be designated by one of the pointer $S_1, S_2, \ldots S_{n-1}, S_n, S_{n+1} \ldots$ and includes two columns. A first of these two columns is a hazard ratio (HR) column and contains hazard ratio ranges which are accessed by a highest combined hazard ratio HR that is determined by the respirator selection component 1000 illustrated in FIG. 10. A second of these two columns is a respirator type column which includes pointers to the Facepiece Database 204, the Filters Database 206, and/or the Respirator Database 207. Accordingly, when a highest combined hazard ratio HR is calculated by the respirator selection component 1000 illustrated in FIG. 10, the calculated highest combined hazard ratio HR is used in the Standards Tables database 205 to determine pointers into the Facepiece Database 204, the Filters Database 206, and/or the Respirator Database 207 as will be explained hereinafter.

Figures 8, 9:
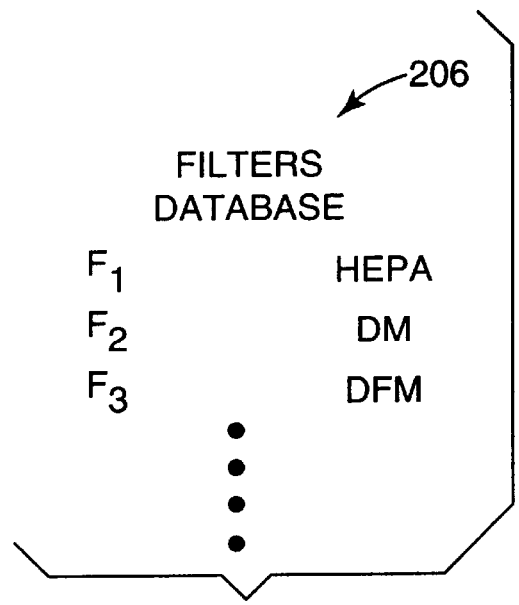

An example of the Filters Database 206 is illustrated in FIG. 8. The Filters Database 206 stores a listing of the filters which are available for the respirators contained in the Respirator Database 207. These filters are stored in the Filters Database 206 in accordance with the filters pointers $F_1, F_2, F_3, \ldots F_{n-1}, F_n, F_{n+1} \ldots$ contained in the Standards Tables Database 205.

Finally, an example of the Respirator Database 207 is illustrated in FIG. 9. The Respirator Database 207 stores a plurality of respirators by name (i.e., by pointer from the Standards Tables database 205) and itself contains pointers to the Facepiece Database 204, the Gas and Vapor Categories Database 202, and the Filters Database 206. Accordingly, when a respirator is pointed to by a pointer from the Standards Tables Database 205, the entry in the Respirator Database 207 for this respirator points to the filter and facepiece to be used in combination with the respirator in order to protect against gases and vapors which are contained in the Gas and Vapor Categories Database 202 and which are pointed to by the Respirator Database 207.

The respirator selection component 1000 of the respirator selection program 118, as illustrated in FIG. 10, is a non-standards based engine. Thus, the respirator selection component 1000 is non-rules based and, therefore, contains substantially none of the standards relating to the selection of respirators. When the respirator selection program 118 is entered by the user who wishes to select a respirator, a block 1002 of the respirator selection component 1000 causes a chemicals screen display to be presented to the user. This chemicals screen display prompts the user to enter the chemical or chemicals against which protection by a respirator is desired. When the user enters the chemical or chemicals in the screen display presented by the block 1002, a block 1004 causes an exposure amounts screen display to be presented to the user. The exposure amounts screen display prompts the user to enter exposure amounts for each of the chemicals which were entered in the chemicals screen display presented to the user by execution of the block 1002. The exposure amounts may be given in parts per million or in any other units specified by the respirator selection program 118.

For each of the chemicals entered in the chemicals screen display presented to the user by execution of the block 1002, and based upon the pointers in the Chemicals Database 201 corresponding to that chemical, a block 1006 fetches the corresponding gas and vapor category from the Gas and Vapor Categories Database 202, the corresponding health effect from the Health Effects Database 203, and the appropriate standards table from the Standards Tables Database 205. The gas and vapor categories, health effects, and standards tables fetched by the block 1006 are stored in a temporary memory 1008.

For example, if the user enters chemical X in the chemicals screen display presented to the user by execution of the block 1002, the block 1006 accesses the chemical X column of the Chemicals Database 201 in order to determine the gas and vapor category pointer, the health effects pointer, and the standards table pointer for chemical X. The block 1006 then fetches the gas and vapor category from the Gas and Vapor Categories Database 202 based upon the gas and vapor category pointer for chemical X as contained in the Chemicals Database 201 and stores the fetched gas and vapor category in the temporary memory 1008; the block 1006 fetches the health effect from the Health Effects Database 203 based upon the health effects pointer for chemical X as contained in the Chemicals Database 201 and stores the fetched health effect in the temporary memory 1008; and, the block 1006 fetches the standards table from the Standards Tables Database 205 based upon the standards tables pointer for chemical X as contained in the Chemicals Database 201 and stores the fetched standards table in the temporary memory 1008. In a similar manner, the block 1006 fetches the gas and vapor categories, the health effects, and the standards tables for the other chemicals entered by the user in the chemicals screen display presented to the user by execution of the block 1002, and stores the fetched gas and vapor categories, the fetched health effects, and the fetched standards table in the temporary memory 1008. The chemicals entered as a result of the chemicals screen display presented to the user by execution of the block 1002 are also stored in the temporary memory 1008.

Thereafter, a block 1010 segments the chemicals stored in the temporary memory 1008 according to health effects. That is, the chemicals stored in the temporary memory 1008 are sorted by health effect so that all chemicals having the same health effect are stored in a common health effects segment. This segmentation of chemicals by health effects is then stored in a temporary memory 1012. The chemicals are segmented by health effects in order to facilitate the hazard ratio calculation process as described hereinafter.

Following segmentation of the chemicals by health effects, a block 1014 calculates the highest combined hazard ratio HR. That is, the block 1014 calculates a hazard ratio for the first chemical (i.e., $chemical_1$) stored in the temporary memory 1012. In order to calculate this hazard ratio, the block 1014 accesses the Chemicals Database 201 for the exposure limit for $chemical_1$, and divides the exposure amount entered in the exposure amount screen display by the user for this chemical by the exposure limit from the Chemicals Database 201 according to following equation:

$$HR_i = \frac{exposure\ amount_i}{exposure\ limit_i} \qquad (1)$$

where i=1 in the case of the first chemical to be so processed. The block 1014 similarly calculates hazard ratios for the other chemicals entered by the user in the chemicals screen display by execution of the block 1002. When all such hazard ratios are calculated, the block 1014 adds all of the hazard ratios resulting from chemicals having the same health effect. For example, if first and second chemicals, as entered by the user in the chemicals screen display by execution of the block 1002, have a first health effect, and if third and fourth chemicals, as entered by the user in the chemicals screen display by execution of the block 1002, have a second health effect, the hazard ratios associated with the first and second chemicals are added together in order to produce a first combined hazard ratio, and the hazard ratios calculated for the third and fourth chemicals are added together in order to produce a second combined hazard ratio. On the other hand, if the first, second, third, and fourth chemicals have the same health effect, the hazard ratios calculated for the first, second, third, and fourth chemicals are added together in order to produce only one combined hazard ratio for these four chemicals.

If more than one combined hazard ratio results from this process because the entered chemicals produce more than one health effect, then the block 1014 picks the highest combined hazard ratio and stores this highest combined hazard ratio in a temporary memory 1016 as the highest combined hazard ratio HR.

A block 1018 selects, from each of the fetched standards tables stored in the temporary memory 1008, the facepiece and the filter corresponding to the highest combined hazard ratio HR stored in the temporary memory 1016. Accordingly, if the user had entered plural chemicals in the chemicals screen display by execution of the block 1002 and these plural chemicals resulted in plural standards tables being fetched by the block 1006 and being stored in the temporary memory 1008, the block 1018 selects a facepiece and a filter from each of these standards tables based upon the highest combined hazard ratio HR stored in the temporary memory 1016.

The result of this processing is that the block 1018 selects plural facepieces and filters if plural chemicals were entered in the chemicals screen display. The block 1018 then sorts the selected facepieces according to effectiveness from highest effectiveness to lowest effectiveness and stores these sorted facepieces in a temporary memory 1020. Similarly, the block 1018 sorts the selected filters according to effectiveness from highest effectiveness to lowest effectiveness and stores these sorted filters in the temporary memory 1020.

A block 1022 accesses the temporary memory 1008, the temporary memory 1020, and the Respirator Database 207 in order to select, from among the facepieces and filters stored in the temporary memory 1020, the respirator, filter, and facepiece combination which, as indicated by the Respirator Database 207, provides the highest degree of effectiveness, and protects against all of the gas and vapor categories stored in the temporary memory 1008. That is, the block 1022 first selects, from among the facepieces and filters stored in the temporary memory 1020, the facepiece and filter which provide the highest degree of effectiveness. The block 1022 then accesses the Respirator Database 207 in order to select the respirator which, when combined with the selected facepiece and filter, protects against all of the gas and vapor categories stored in the temporary memory 1008 and provides adequate facepiece and filter protection. The block 1022 may be arranged to select no respirator if the highest combined hazard ratio HR is less than a predetermined value, e.g., if the highest combined hazard ratio HR is less than one.

A block 1024 then displays this selected respirator, facepiece, and filter to the user.

Accordingly, the present invention provides a set of interacting databases 201–207 which contain information on chemicals, health effects, respirators, and government standards. The respirator selection component 1000 illustrated in FIG. 10 integrates with the databases 201–207 in order to provide a respirator selection solution. Because the health effects, chemical interactions, and government standards are built as databases rather than into rules, they are more easily upgraded as standards change and they also allow multiple versions to be built which handle regulations from different countries. Moreover, the use of both health effects and chemical interactions in the selection of a respirator is important in arriving at an accurate respirator solution.

Certain modifications of the present invention have been discussed above. Other modifications will occur to those practicing in the art of the present invention. For example, more or fewer databases may be used in the database component 200 of the respirator selection program 118.

Also, examples of pointers which point from specific databases into other specific databases have been disclosed herein. It should be understood, however, that these pointers are illustrative, such that pointers may point from any of the databases disclosed herein to any of the other databases.

Moreover, examples of the Chemicals Database 201, the Gas and Vapor Categories Database 202, the Health Effects Database 203, the Facepiece Database 204, the Standards Tables Database 205, the Filters Database 206, and the Respirator Database 207 have been disclosed herein. However, these databases may contain more or different data than that shown.

Furthermore, as described above, the block 1022 may be arranged to select no respirator if the highest combined hazard ratio HR is less than a predetermined value. Alternatively, the block 1014 or the block 1018 may be arranged to terminate the respirator selection process if the highest combined hazard ratio HR is less than a predetermined value.

Accordingly, the description of the present invention is to be construed as illustrative only and is for the purpose of teaching those skilled in the art the best mode of carrying out the invention. The details may be varied substantially without departing from the spirit of the invention, and the exclusive use of all modifications which are within the scope of the appended claims is reserved.

What is claimed is:

1. A method of selecting a respirator comprising the steps, performed by a data processing system, of:

a) executing program code in the data processing system in order to determine a health effect of a first chemical;

b) executing program code in the data processing system in order to determine a health effect of a second chemical; and, c) executing program code in the data processing system in order to select a respirator based upon the health effects of the first and second chemicals.

2. The method of claim 1 wherein step a) comprises the step of determining a first hazard index related to the first chemical, wherein step b) comprises the step of determining a second hazard index related to the second chemical, and wherein step c) comprises the step of selecting the respirator based upon the first and second hazard indices.

3. The method of claim 2 wherein the step of selecting the respirator based upon the first and second hazard indices comprises the following steps:

summing the first and second hazard indices if the health effects of the first and second chemicals are the same, thereby producing a combined hazard index; and, selecting the respirator based upon the combined hazard index.

4. The method of claim 2 wherein the step of selecting the respirator based upon the first and second hazard indices comprises the following steps:

selecting a higher of the first and second hazard indices if the health effects of the first and second chemicals are not the same, thereby producing a highest hazard index; and, selecting the respirator based upon the highest hazard index.

5. The method of claim 2 wherein the step of determining the first hazard index comprises the step of determining a first hazard ratio based upon a ratio of an exposure amount for the first chemical and an exposure limit for the first chemical, and wherein the step of determining the second hazard index comprises the step of determining a second hazard ratio based upon a ratio of an exposure amount for the second chemical and an exposure limit for the second chemical.

6. The method of claim 5 wherein the step of selecting the respirator based upon the first and second hazard indices comprises the following steps:

summing the first and second hazard ratios if the health effects of the first and second chemicals are the same, thereby producing a combined hazard ratio; and, selecting the respirator based upon the combined hazard ratio.

7. The method of claim 6 wherein the step of selecting the respirator based upon the combined hazard ratio comprises the step of selecting no respirator if the combined hazard ratio is less than a predetermined value.

8. The method of claim 5 wherein the step of selecting the respirator based upon the first and second hazard indices comprises the following steps:

selecting a higher of the first and second hazard ratios if the health effects of the first and second chemicals are not the same, thereby producing a highest hazard ratio; and, selecting the respirator based upon the highest hazard ratio.

9. The method of claim 8 wherein the step of selecting the respirator based upon the highest hazard ratio comprises the step of selecting no respirator if the highest hazard ratio is less than a predetermined value.

10. The method of claim 5 wherein the step of selecting the respirator based upon the first and second hazard indices comprises the step of selecting a facepiece and a filter based upon the first and second hazard ratios.

11. The method of claim 10 wherein the step of selecting a facepiece and a filter based upon the first and second hazard ratios comprises the step of selecting the respirator based upon the facepiece and filter.

12. The method of claim 11 wherein the step of selecting the respirator based upon the facepiece and filter comprises the step of selecting the respirator based upon the facepiece, the filter, and a gas and/or vapor.

13. The method of claim 2 further comprising the step of executing program code in the data processing system in order to determine a health effect of a third chemical and in order to determine a third hazard index related to the third chemical, and wherein step c) comprises the following steps:

summing the first and second hazard indices if the health effects of the first and second chemicals are the same, thereby producing a combined hazard index; and, selecting a higher of the combined hazard index and the third hazard index if the health effects of the first and second chemicals are different from the health effect of the third chemical, thereby producing a highest combined hazard index; and, selecting the respirator based upon the highest combined hazard index.

14. A computer readable storage medium having program code stored thereon, wherein the program code contains a chemicals database, a standards database, and a respirator database, wherein the chemicals database contains data on chemicals which may require the use of respirators, wherein the standards database contains data on respirator selection related to the chemicals contained in the chemicals database, and wherein the program code further contains a non-standards based engine which, when executed, performs the steps of (i) accepting a chemical which is entered by a user, (ii) accepting an exposure amount which is entered by the user, and (iii) selecting a respirator based upon the chemicals database, the standards database, the respirator database, the chemical which is entered by the user, and the exposure amount which is entered by the user.

15. The computer readable storage medium of claim 14 further comprising a facepiece database and a filter database, wherein the standards database contains pointers into the facepiece and filter databases, and wherein the non-standards based engine, when executed, performs the steps of (i) extracting a portion of the standards database dependent upon the chemical which is entered by the user, (ii) determining a hazard index based upon the chemical and the exposure amount which is entered by the user, (iii) indexing the extracted portion of the standards database based upon the hazard index to determine pointers into the facepiece and filter databases, and (iv) selecting a respirator from the respirator database based upon the pointers into the facepiece and filter databases.

16. The computer readable storage medium of claim 15 further comprising a gas and vapor database, wherein the chemicals database contains pointers into the gas and vapor database, and wherein the non-standards based engine, when executed, selects a respirator from the respirator database which is based upon the pointers into the facepiece and filter databases and which protects against a gas and vapor corresponding to the chemical.

17. The computer readable storage medium of claim 15 wherein the step of determining the hazard index based upon the chemical and the exposure amount which is entered by the user comprises the step of:

determining a hazard ratio based upon a ratio of the exposure amount which is entered by the user and an exposure limit which is stored in the chemicals database and which relates to the chemical.

18. The computer readable storage medium of claim 17 wherein the step of selecting the respirator comprises the step of:

selecting no respirator if the hazard ratio is less than a predetermined value.

19. The computer readable storage medium of claim 17 further comprising a gas and vapor database, wherein the chemicals database contains pointers into the gas and vapor database, and wherein the non-standards based engine, when executed, selects a respirator from the respirator database which is based upon the pointers into the facepiece and filter databases and which protects against gas and vapor corresponding to the chemical.

20. A computer readable storage medium having program code stored thereon, wherein the program code contains a chemicals database, a health effects database, a standards database, and a respirator database, wherein the chemicals database contains data on chemicals which may require the use of respirators, wherein the chemicals database contains pointers to the health effects database, wherein the health effects database contains health effects resulting from exposure to the chemicals in the chemical database, and wherein the program code further contains a non-standards based engine which, when executed, performs the steps of (a) accepting first and second chemicals which are entered by a user, and (b) selecting a respirator based upon the chemicals database, the health effects database, the standards database, the respirator database, and the first and second chemicals which are entered by the user.

21. The computer readable storage medium of claim 20 wherein step (b) comprises the steps of:

accepting corresponding first and second exposure amounts which correspond to the first and second chemicals and which are entered by the user; and, selecting a respirator based upon the chemicals database, the health effects database, the standards database, the respirator database, the first and second chemicals which are entered by the user, and the first and second exposure amounts which are entered by the user.

22. The computer readable storage medium of claim 21 wherein step (c) further comprises the steps of:

determining a first hazard index related to the first chemical and the first exposure amount;

determining a second hazard index related to the second chemical and the second exposure amount; and, selecting the respirator based upon the first and second hazard indices, the chemicals database, the health effects database, the standards database, and the respirator database.

23. The computer readable storage medium of claim 22 wherein the step of selecting the respirator based upon the first and second hazard indices, the chemicals database, the health effects database, the standards database, and the respirator database comprises the following steps:

summing the first and second hazard indices if the health effects to which the first and second chemicals point are the same, thereby producing a combined hazard index; and, selecting the respirator based upon the combined hazard index, the standards database, and the respirator database.

24. The computer readable storage medium of claim 22 wherein the step of selecting the respirator based upon the first and second hazard indices, the chemicals database, the health effects database, the standards database, and the respirator database comprises the following steps:

selecting a higher of the first and second hazard indices if the health effects to which the first and second chemicals point are not the same, thereby producing a highest hazard index; and, selecting the respirator based upon the highest hazard index, the standards database, and the respirator database.

25. The computer readable storage medium of claim 22 wherein the step of determining the first hazard index comprises the step of determining a first hazard ratio based upon a ratio of the first exposure amount corresponding to the first chemical which is entered by the user and an exposure limit for the first chemical which is stored in the chemicals database, and wherein the step of determining the second hazard index comprises the step of determining a second hazard ratio based upon a ratio of the second exposure amount corresponding to the second chemical which is entered by the user and an exposure limit for the second chemical which is stored in the chemicals database.

26. The computer readable storage medium of claim 25 wherein the step of selecting the respirator based upon the first and second hazard indices, the chemicals database, the health effects database, the standards database, and the respirator database comprises the following steps:

summing the first and second hazard ratios if the health effects to which the first and second chemicals point are the same, thereby producing a combined hazard ratio; and, selecting the respirator based upon the combined hazard ratio, the standards database, and the respirator database.

27. The computer readable storage medium of claim 26 wherein the step of selecting the respirator based upon the combined hazard ratio, the standards database, and the respirator database comprises the step of:

selecting no respirator if the combined hazard ratio is less than a predetermined value.

28. The computer readable storage medium of claim 25 wherein the step of selecting the respirator based upon the first and second hazard indices, the chemicals database, the health effects database, the standards database, and the respirator database comprises the following steps:

selecting a higher of the first and second hazard ratios if the health effects to which the first and second chemicals point are not the same, thereby producing a highest hazard ratio; and, selecting the respirator based upon the highest hazard ratio, the standards database, and the respirator database.

29. The computer readable storage medium of claim 28 wherein the step of selecting the respirator based upon the highest hazard ratio, the standards database, and the respirator database comprises the step of:

selecting no respirator if the highest hazard ratio is less than a predetermined value.

30. The computer readable storage medium of claim 25 further comprising a facepiece database and a filter database, wherein the standards database contains pointers into the facepiece and filter databases, and wherein the step of selecting the respirator based upon the first and second hazard indices, the chemicals database, the health effects database, the standards database, and the respirator database comprises the steps of:

extracting portions of the standards database dependent upon the first and second chemicals which are entered by the user;

indexing the extracted portions of the standards database based upon the first and second hazard ratios in order to determine pointers into the facepiece and filter databases; and, selecting a respirator from the respirator database based upon the pointers into the facepiece and filter databases.

31. The computer readable storage medium of claim 30 wherein the step of selecting a respirator from the respirator database based upon the pointers into the facepiece and filter databases comprises the further step of:

selecting a facepiece and a filter based upon the first and second hazard ratios and the pointers from the respirator database to the facepiece and filter databases.

32. The computer readable storage medium of claim 31 wherein the step of selecting a facepiece and a filter comprises the step of:

selecting a respirator which protects against gases and vapors corresponding to the first and second chemicals which are entered by the user.

33. The computer readable storage medium of claim 32 wherein the step of selecting a facepiece and a filter comprises the step of:

selecting a respirator, facepiece, and filter combination which protects against gases and vapors corresponding to the first and second chemicals which are entered by the user.

34. The computer readable storage medium of claim 30 wherein the step of selecting the respirator comprises the following steps:

summing the first and second hazard ratios if the health effects to which the first and second chemicals point are the same, thereby producing a combined hazard ratio;

indexing the standards database based upon the combined hazard ratio in order to determine pointers into the facepiece and filter databases; and, selecting a respirator from the respirator database based upon the pointers into the facepiece and filter database.

35. The computer readable storage medium of claim 30 wherein the step of selecting the respirator comprises the following steps:

selecting a higher of the first and second hazard ratios if the health effects to which the first and second chemicals point are not the same, thereby producing a highest hazard ratio;

indexing the standards database based upon the highest hazard ratio in order to determine pointers into the facepiece and filter databases; and, selecting a respirator from the respirator database based upon the pointers into the facepiece and filter database.

36. The computer readable storage medium of claim 22 further comprising the steps of:

accepting a third chemical which is entered by a user;

determining a third hazard index related to the first chemical and the first exposure amount;

summing the first and second hazard indices when the health effects to which the first and second chemicals point are the same, thereby producing a combined hazard index;

selecting a higher of the combined hazard index and the third hazard index if the health effect to which the first and second chemicals point is different than the health effect to which the third chemical points, thereby producing a highest combined hazard index;

indexing the standards database based upon the highest combined hazard index in order to determine pointers into the facepiece and filter databases; and, selecting a respirator from the respirator database based upon the pointers into the facepiece and filter database.

37. The computer readable storage medium of claim 36 wherein the step of selecting a respirator from the respirator database based upon the pointers into the facepiece and filter database comprises the steps of:

extracting portions of the standards database dependent upon the first, second, and third chemicals which are entered by the user;

indexing the extracted portions of the standards database based upon the highest combined hazard index in order to determine pointers into the facepiece and filter databases; and, selecting a respirator from the respirator database based upon the pointers into the facepiece and filter databases.

38. An article of manufacture comprising:

a computer readable storage medium; and, program code stored on the computer readable storage medium, wherein the program code contains a database and a non-standards based engine, wherein the non-standards based engine, when executed, performs the steps of (a) accepting first and second chemicals which are entered by a user, (b) accepting first and second exposure amounts which correspond to the first and second chemicals and which are entered by the user, and (c) selecting a respirator based upon the database, the first and second chemicals which are entered by the user, and the first and second exposure amounts which are entered by the user.

39. The computer readable storage medium of claim 38 wherein step (c) comprises the steps of:

determining a first hazard index related to the first chemical and the first exposure amount;

determining a second hazard index related to the second chemical and the second exposure amount; and, selecting the respirator based upon the first and second hazard indices and the database.

40. The computer readable storage medium of claim 39 wherein the step of selecting the respirator based upon the first and second hazard indices and the database comprises the following steps:

summing the first and second hazard indices, thereby producing a combined hazard index; and, selecting the respirator based upon the combined hazard index and the database.

41. The computer readable storage medium of claim 39 wherein the step of selecting the respirator based upon the first and second hazard indices and the database comprises the following steps:

selecting a higher of the first and second hazard indices, thereby producing a highest hazard index; and, selecting the respirator based upon the highest hazard index and the database.

42. The computer readable storage medium of claim 39 wherein the step of determining the first hazard index comprises the step of determining a first hazard ratio based upon a ratio of the first exposure amount corresponding to the first chemical which is entered by the user and an exposure limit for the first chemical which is stored in the database, and wherein the step of determining the second hazard index comprises the step of determining a second hazard ratio based upon a ratio of the second exposure amount for the second chemical which is entered by the user and an exposure limit for the second chemical which is stored in the database.

43. The computer readable storage medium of claim 42 wherein the step of selecting the respirator comprises the following steps:

summing the first and second hazard ratios, thereby producing a combined hazard ratio; and, selecting the respirator based upon the combined hazard ratio and the database.

44. The computer readable storage medium of claim 43 wherein the step of selecting the respirator based upon the combined hazard ratio and the database comprises the step of:

selecting no respirator if the combined hazard ratio is less than a predetermined value.

45. The computer readable storage medium of claim 42 wherein the step of selecting the respirator comprises the following steps:

selecting a higher of the first and second hazard ratios, thereby producing a highest hazard ratio; and, selecting the respirator based upon the highest hazard ratio and the database.

46. The computer readable storage medium of claim 45 wherein the step of selecting the respirator based upon the highest hazard ratio and the database comprises the step of:

selecting no respirator if the highest hazard ratio is less than a predetermined value.

47. The computer readable storage medium of claim 39 further comprising the steps of:

accepting a third chemical which is input by a user;

determining a third hazard index related to the first chemical and the first exposure amount;

summing the first and second hazard indices, thereby producing a combined hazard index;

selecting a higher of the combined hazard index and the third hazard index, thereby producing a highest combined hazard index; and, selecting a respirator based upon the database and the highest combined hazard index.

48. A computer readable storage medium having program code stored thereon, wherein the program code includes a database containing data on chemicals and respirators, and wherein the program code further includes a non-standards based engine which, when executed, performs the steps of (a) accepting first and second chemicals which are entered by a user, and (b) selecting a respirator based upon the database and the first and second chemicals which are entered by the user.

* * * * *